United States Patent [19]

Iijima et al.

[11] Patent Number: 4,612,187

[45] Date of Patent: Sep. 16, 1986

[54] ORYZANOL-CONTAINING SOFT CAPSULE

[75] Inventors: Takeo Iijima, Koushoku; Hiroyuki Sano, Ueda, both of Japan

[73] Assignee: Nisshin Chemicals Co., Ltd., Japan

[21] Appl. No.: 668,663

[22] Filed: Nov. 6, 1984

Related U.S. Application Data

[63] Continuation of Ser. No. 488,790, Apr. 26, 1983, abandoned.

[51] Int. Cl.$^4$ ................................ A61K 9/48
[52] U.S. Cl. ...................... 424/16; 424/37; 424/14; 514/943
[58] Field of Search ............ 424/16, 37, 172; 514/943

[56] References Cited

FOREIGN PATENT DOCUMENTS 7310522  4/1973  Japan .
7829916  3/1978  Japan .
58-103315  6/1983  Japan .
58-128141  7/1983  Japan .

OTHER PUBLICATIONS

Lachman et al, "The Theory & Practice of Industrial Pharmacy", 2nd Ed., Lea & Febiger, 1976, pp. 406–407.
Physicians Desk Reference, 1981, p. 405.
Shinomura et al, Effect of γ-Oryzanol on Serum TSH Concentrations in 1° Hypothyroidism Endocrin, Japan, 27(1)83–83 (1980).

*Primary Examiner*—Albert T. Meyers
*Assistant Examiner*—C. Joseph Faraci
*Attorney, Agent, or Firm*—Abelman Frayne Rezac & Schwab

[57] ABSTRACT

A soft capsule containing as active ingredient γ-oryzanol alone or oryzanol in combination with riboflavin butyrate is described. The shelf life of this composition is increased without precipitation of the ingredients thereof.

1 Claim, No Drawings

ORYZANOL-CONTAINING SOFT CAPSULE

This is a continuation of application Ser. No. 488,790, filed Apr. 26, 1983, now abandoned.

The present invention relates to a soft capsule containing as an active ingredient γ-oryzanol alone or γ-oryzanol in combination with the butyric ester of riboflavin.

γ-Oryzanol is an oryzayl alcohol ester of ferulic acid having an antioxidant action. It is known that γ-oryzanol is effective against climacteric melancholia and the butyric ester of riboflavin is also effective in preventing arteriosclerosis.

Unfortunately, however, the solubility of γ-oryzanol in oil is 10 mg/g (oil) and that of the butyric ester of riboflavin is 0.84×7 mg/g (oil). Therefore, these compounds crystallize out when filled in a soft capsule in an amount enough for practical use (e.g., 45.5 mg/g (oil)), and the resulting crystals make the capsule opaque, decreasing their commercial value.

In order to overcome these disadvantages, the present inventors carried out a series of studies. As a result, they found that the solubility in oil is greatly increased when γ-oryzanol or a combination of γ-oryzanol and the butyric ester of riboflavin is incorporated with a surface active agent.

Accordingly, the gist of the present invention resides in a soft capsule which comprises encapsulated within the film-forming agent (a) γ-oryzanol alone or γ-oryzanol in combination with the butyric ester of riboflavin, (b) one or more than one kind of surface active agent selected from the group consisting of sorbitan monolaurate, sorbitan sesquioleate, and sorbitan monooleate, and (c) oil.

The soft capsule of this invention is produced in the following steps. At first, γ-oryzanol alone or a composition composed of γ-oryzanol and butyric ester of riboflavin, and one or more than one kind of surface active agent selected from the above-mentioned three kinds are mixed with oil. The resulting mixture is placed between two ribbons made of the film-forming agent, and the ribbons are pressed against each other by dies, whereby the soft capsule is formed. The capsule forming step may be carried out by the automatic rotary process, semiautomatic Norton machine, or manual plate process. The soft capsule may be spherical, elliptic, or other shapes.

The γ-oryzanol used in this invention is commercially available. The preferred γ-Oryzanol is composed of 25 to 50% of campesterol, 15 to 25% of β-sitosterol, 15 to 30% of cycloartenol, and 10 to 40% of 2,4-methylenecycloartanol. γ-Oryzanol having such a composition can be prepared by extracting so-called "foots" with n-hexane, condensing the extract, extracting with acetone, and cooling the extract for crystallization. The γ-oryzanol to be filled in the soft capsule is used in an amount of 1 to 7%, preferably 2 to 5%, based on the weight of oil.

The butyric ester of riboflavin used in this invention is commercially available, and it is used in an amount of 1 to 7%, preferably 2 to 5%, based on the weight of oil.

The sorbitan monolaurate, sorbitan sesquioleate, and sorbitan monooleate used in this invention may be selected from commercial ones. A preferred sorbitan monolaurate is one in which the content of total free polyol is reduced to 2 to 5%. A preferred sorbitan sesquioleate is one in which the content of total free polyol has been reduced to 0.3 to 1.2%. A preferred sorbitan monooleate is one in which the content of total free polyol is 2 to 5%. These surface active agents are incorporated in an amount of 5 to 50%, preferably 10 to 35%, based on the weight of the drug to be filled in the soft capsule.

The oil used in this invention includes, for example, tocopherol and derivatives thereof, wheat germ oil, safflower oil, soybean oil, neutral oil, cottonseed oil, rapeseed oil, corn oil, and peanut oil. The oil may be incorporated with additives such as sweetener and flavor, as required.

The film-forming agent for the soft capsule includes, for example, gelatin. In order to prevent moisture in the air from entering the soft capsule, the gelatin should preferably be incorporated with sorbitol in an amount of 10 to 30%, more suitably 15 to 25%.

The soft capsule of this invention is characerized by that γ-oryzanol or a drug composed of γ-oryzanol and butyric ester of riboflavin does not crystallize out even when it is dissolved in oil in an amount exceeding the ordinary solubility. Thus, the soft capsule of this invention is stable over a long period of time at normal temperature.

The invention is now described in more detail with reference to the following examples.

EXAMPLE 1

The compositions to be filled in soft capsules were prepared by mixing γ-oryzanol, sorbitan monolaurate, sorbitan sesquioleate, wheat germ oil, and d-α-tocopherol acetate in the ratios shown in Table 1.

The film-forming agent was prepared by mixing 116.3 mg of gelatin, 51.1 mg of concentrated glycerin, 1.0 mg of methyl p-hydroxybenzoate, 0.4 mg of propyl p-hydroxybenzoate, and 1.2 mg of purified water.

Soft capsules were produced from the above-mentioned drugs and film-forming agent using an automatic rotary capsule filling machine (built by Liner Co.)

The resulting soft capsules were stored under the condition of 40° C. and 75% RH for 2 months and under the condition of 20° C. and 95% RH for 2 months. The change after storage was observed. The results are shown in Table 2. In the table, "Degree of crystallization" is in accordance with the following criterion.

−: No crystallization
+: One to two small crystals on the inside of the capsule wall
++: Crystallization all over the inside of the capsule wall
+++: Crystallization entirely in the capsule

TABLE 1

Compositions of Drugs Filled in Soft Capsules
(Unit: mg)

| Components | A | B | C | D | E | F | G | H |
|---|---|---|---|---|---|---|---|---|
| γ-Oryzanol | 10 | 10* | 10* | 10* | 10 | 10* | 10* | 10* |
| Sorbitan monolaurate | — | — | 50** | 50** | 50** | 50 | — | 50 |

TABLE 1-continued

| | Compositions of Drugs Filled in Soft Capsules (Unit: mg) Compositions | | | | | | | |
|---|---|---|---|---|---|---|---|---|
| Components | A | B | C | D | E | F | G | H |
| Sorbitan sesquioleate | 50⁻ | 50⁻ | — | 50⁻ | 50⁻ | — | 50 | 50 |
| Wheat germ oil | 180 | 180 | 180 | 130 | 130 | 180 | 180 | 180 |
| d-α-Tocopherol acetate | 100 | 100 | 100 | 100 | 100 | 100 | 100 | 100 |

*γ-Oryzanol composed of 32.02% of campesterol, 25.73% of β-sitosterol, 24.47% of cycloartenol, and 14.60% of 2,4-methylenecycloartanol.
**Sorbitan monolaurate containing 2.45% of total free polyol.
⁻Sorbitan sesquioleate containing 0.52% of total free polyol.

TABLE 2

| | | Results of Storage of Soft Capsules | | | | | |
|---|---|---|---|---|---|---|---|
| | | Immediately after production | | | After storage | | |
| Compositions | Storage condition | External appearance | Degree of crystallization | Microscopic examination | External appearance | Degree and time of crystallization | Microscopic examination |
| A | 40° C. & 75% RH | Yellowish transparent | — | — | Yellowish transparent | — | — |
| B | | Yellowish transparent | — | — | Yellowish transparent | — | — |
| C | | Yellowish transparent | — | — | Yellowish transparent | — | — |
| D | | Yellowish transparent | — | — | Yellowish transparent | — | — |
| E | | Yellowish transparent | — | — | Yellowish transparent | — | — |
| F | | Yellowish transparent | — | — | Yellowish transparent | — | — |
| G | | Yellowish transparent | — | — | Yellowish transparent | — | — |
| H | | Yellowish transparent | — | — | Yellowish transparent | — | — |
| A | 20° C. & 95% RH | Yellowish transparent | — | — | Yellowish oil crystallized | ++ (1 month) | γ-oryzanol |
| B | | Yellowish transparent | — | — | Yellowish transparent | — | — |
| C | | Yellowish transparent | — | — | Yellowish oil crystallized | ++ (1 month) | γ-oryzanol |
| D | | Yellowish transparent | — | — | Yellowish oil crystallized | — | — |
| E | | Yellowish transparent | — | — | Yellowish oil crystallized | ++ (2 months) | γ-oryzanol |
| F | | Yellowish transparent | — | Polyol | Yellowish oil crystallized | +++ (2 months) | γ-oryzanol polyol |
| G | | Yellowish transparent | — | Polyol | Yellowish oil crystallized | +++ (2 months) | γ-oryzanol polyol |
| H | | Yellowish transparent | — | Polyol | Yellowish oil crystallized | +++ (2 months) | γ-oryzanol polyol |

The storage for two weeks at 20° C. and 95% RH corresponds to the storage for one year at room temperature. Therefore, even in the case of the soft capsule in which crystallization occurred in a degree of +++ (2 months), stable storage will be ensured at room temperature for more than 2 years.

EXAMPLE 2

The compositions to be filled in soft capsules were prepared by mixing γ-oryzanol, butyric ester of riboflavin (abbreviated as VB₂ hereinafter), sorbitan monolaurate, sorbitan sesquioleate, wheat germ oil, and d-α-tocopherol acetate in the ratios shown in Table 3.

Soft capsules of this invention and soft capsules for comparison were produced from the above-mentioned drugs in the same way as in Example 1.

The resulting soft capsules were stored at room temperature for 2 years and also under the condition of 40° C. and 75% RH for 6 months. The change after storage was observed. The results are shown in Table 4. In the table, "Degree of crystallization" is in accordance with the criterion used in Example 1.

TABLE 3

| | Compositions of Drugs Filled in Soft Capsules (Unit: mg) | | | | | | | |
|---|---|---|---|---|---|---|---|---|
| | Compositions of this invention | | | Compositions for comparison | | | | |
| Components | I | J | K | L | M | N | O | P |
| γ-Oryzanol | 10 | 10 | 10* | 10 | 10 | 10 | 10 | 10 |
| VB₂ | 10 | 10 | 10 | 10 | 10 | 10 | — | — |
| Sorbitan monolaurate | 50 | 50** | 50** | — | — | — | — | — |
| Sorbitan sesquioleate | 50 | 50⁺ | 50⁺ | — | — | — | — | — |
| Wheat germ oil | 120 | 120 | 120 | 220 | 170 | 170 | 170 | 170 |

TABLE 3-continued

Compositions of Drugs Filled in Soft Capsules
(Unit: mg)

| Components | Compositions of this invention | | | Compositions for comparison | | | | |
|---|---|---|---|---|---|---|---|---|
| | I | J | K | L | M | N | O | P |
| d-α-Tocopherol acetate | 100 | 100 | 100 | 100 | 100 | 100 | 100 | 100 |
| Nikkol BCO-60 (Nikko Chemicals Co.) | — | — | — | — | 100 | — | 60 | — |
| Nikkol TO-10 (Nikko Chemicals Co.) | — | — | — | — | — | 100 | — | 60 |

*γ-Oryzanol composed of 32.02% of campesterol, 25.73% of β-sitosterol, 24.47% of cycloartenol, and 14.60% of 2,4-methylenecycloartanol.
**Sorbitan monolaurate containing 2% of total free polyol.
+Sorbitan sesquioleate containing 0.52% of total free polyol.

TABLE 4

Results of Storage of Soft Capsules

| Composition | Storage condition | Immediately after production | | | After storage | | |
|---|---|---|---|---|---|---|---|
| | | External appearance | Degree of crystallization | Microscopic examination | External appearance | Degree and time of crystallization | Microscopic examination |
| I | Room temperature | Orange red transparent | — | Polyol | Orange red oil crystallized | + | Polyol γ-oryzanol |
| J | | Orange red transparent | — | — | Orange red transparent | — | — |
| K | | Orange red transparent | — | — | Orange red transparent | — | — |
| L | | Orange red transparent | — | — | Orange red oil crystallized | +++ (10 days) | γ-oryzanol $VB_2$ |
| M | | Orange red transparent | — | — | Brown oil crystallized | +++ (13 days) | $VB_2$ |
| N | | Orange red transparent | — | — | Brown oil crystallized | +++ (13 days) | $VB_2$ |
| O | | Orange red transparent | — | — | Orange red oil crystallized | +++ (10 days) | γ-oryzanol |
| P | | Orange red transparent | — | — | Orange red oil crystallized | +++ (10 days) | γ-oryzanol |
| I | 40° C. & 75% RH | Yellowish transparent | — | Polyol | Orange red transparent | — | — |
| J | | Yellowish transparent | — | — | Orange red transparent | — | — |
| K | | Yellowish transparent | — | — | Orange red transparent | — | — |
| L | | Yellowish transparent | — | — | Orange red oil crystallized | ++ (10 days) | $VB_2$ |
| M | | Yellowish transparent | — | — | Brown oil crystallized | ++ (30 days) | $VB_2$ |
| N | | Yellowish transparent | — | — | Brown oil crystallized | ++ (30 days) | $VB_2$ |
| O | | Yellowish transparent | — | — | Orange red oil crystallized | +++ (10 days) | γ-oryzanol |
| P | | Yellowish transparent | — | — | Orange red oil crystallized | +++ (10 days) | γ-oryzanol |

EXAMPLE 3

The compositions to be filled in soft capsules were prepared by mixing γ-oryzanol, $VB_2$, sorbitan monolaurate, sorbitan sesquioleate, wheat germ oil, and d-α-tocopherol acetate in the ratios shown in Table 5.

Soft capsules of this invention and soft capsules for comparison were produced from the above-mentioned drugs in the same way as in Example 1.

The resulting soft capsules were stored under the condition of 20° C. and 85% RH for 2 months. The results are shown in Table 6. In the table, "Degree of crystallization" is in accordance with the criterion used in Example 1.

TABLE 5

Compositions of Drugs Filled in Soft Capsules
(Unit: mg)

| Components | Compositions of this invention | | | Compositions for comparison | |
|---|---|---|---|---|---|
| | Q | R | S | T | U |
| γ-Oryzanol* | 5 | 10 | 10 | — | — |
| $VB_2$ | 10 | 5 | 10 | 10 | 10 |
| Sorbitan monolaurate** | 50 | 50 | 100 | 50 | 50 |
| Sorbitan sesquioleate+ | 50 | 50 | 100 | 50 | 50 |
| Wheat germ oil | 125 | 125 | 125 | 110 | 125 |
| d-α-Tocopherol acetate | 100 | 100 | 100 | 100 | 100 |

*γ-Oryzanol composed of 32.02% of campesterol, 25.73% of β-sitosterol, 24.47% of cycloartenol, and 14.60% of 2,4-methylenecycloartanol.
**Sorbitan monolaurate containing 2.45% of total free polyol.
+Sorbitan sesquioleate containing 0.52% of total free polyol.

TABLE 6

Results of Storage of Soft Capsules

| Composition | Immediately after production | | | After storage | | |
|---|---|---|---|---|---|---|
| | External appearance | Degree of crystallization | Microscopic examination | External appearance | Degree and time of crystallization | Microscopic examination |
| Q | Orange red transparent | — | — | Orange red transparent | — | — |
| R | Orange red transparent | — | — | Orange red transparent | — | — |
| S | Orange red transparent | — | — | Orange red oil crystallized | + (2 months) | γ-oryzanol |
| T | Orange red transparent | — | — | Orange red oil crystallized | ++ (10 days) | VB$_2$ |
| U | Orange red transparent | — | — | Orange red oil crystallized | ++ (10 days) | VB$_2$ |

The above-mentioned results indicate that the soft capsule of this invention can be stored at room temperature for more than 2 years, and that VB$_2$ crystallizes out in the soft capsule for comparison during storage at room temperature within 1 year.

EXAMPLE 4

Soft capsules were produced in the same way as in Example 1 from the compositions A to H prepared in Example 1 and the film-forming agent prepared by mixing 116.3 mg of gelatin, 25.0 mg of concentrated glycerin, 26.1 mg of sorbitol, 0.4 mg of methyl p-hydroxybenzoate, and 1.2 mg of purified water.

The resulting soft capsules were stored under the condition of 40° C. and 75% RH for 2 months and the condition of 20° C. and 95% RH for 2 months. The results are shown in Table 7. In the table, "Degree of crystallization" is in accordance with the criterion used in Example 1.

TABLE 7

Results of Storage of Soft Capsules

| Composition | Storage condition | External appearance | Degree and time of crystallization | Microscopic examination |
|---|---|---|---|---|
| A | 40° C. & 75% RH | Yellowish transparent | — | — |
| B | | Yellowish transparent | — | — |
| C | | Yellowish transparent | — | — |
| D | | Yellowish transparent | — | — |
| E | | Yellowish transparent | — | — |
| F | | Yellowish transparent | — | — |
| G | | Yellowish transparent | — | — |
| H | | Yellowish transparent | — | — |
| A | 20° C. & 95% RH | Yellowish oil crystallized | + (1 month) | γ-oryzanol |
| B | | Yellowish transparent | — | — |
| C | | Yellowish oil crystallized | ++ (1 month) | γ-oryzanol |
| D | | Yellowish transparent | — | — |
| E | | Yellowish transparent | + (2 months) | γ-oryzanol |
| F | | Yellowish transparent | + (2 months) | γ-oryzanol polyol |
| G | | Yellowish transparent | + (2 months) | γ-oryzanol polyol |
| H | | Yellowish transparent | + (2 months) | γ-oryzanol polyol |

The above results indicate that the capsules of this invention can be stored stably at room temperature without crystallization.

EXAMPLE 5

Soft capsules were produced in the same way as in Example 1 from the compositions I to P prepared in Example 2 and the film-forming agent prepared in Example 4. The resulting soft capsules were stored at room temperature for two years and under the condition of 40° C. and 75% RH for 6 months. The results are shown in Table 8. In the table, "Degree of crystallization" is in accordance with the criterion used in Example 1.

TABLE 8

Results of Storage of Soft Capsules

| Composition | Storage condition | Immediately after production | | | After storage | | |
|---|---|---|---|---|---|---|---|
| | | External appearance | Degree of crystallization | Microscopic examination | External appearance | Degree and time of crystallization | Microscopic examination |
| I | Room temperature | Orange red transparent | — | — | Orange red transparent | — | — |
| J | | Orange red transparent | — | — | Orange red transparent | — | — |
| K | | Orange red transparent | — | — | Orange red transparent | — | — |
| L | | Orange red transparent | — | — | Orange red oil crystallized | +++ (10 days) | γ-oryzanol VB$_2$ |
| M | | Orange red transparent | — | — | Brown oil crystallized | +++ (13 days) | VB$_2$ |
| N | | Orange red transparent | — | — | Brown oil crystallized | +++ (13 days) | VB$_2$ |

TABLE 8-continued

Results of Storage of Soft Capsules

| Composition | Storage condition | Immediately after production | | | After storage | | |
|---|---|---|---|---|---|---|---|
| | | External appearance | Degree of crystallization | Microscopic examination | External appearance | Degree and time of crystallization | Microscopic examination |
| O | | Orange red transparent | — | — | Orange red oil crystallized | +++ (10 days) | γ-oryzanol |
| P | | Orange red transparent | — | — | Orange red oil crystallized | +++ (10 days) | γ-oryzanol |
| I | 40° C. & 75% RH | Orange red transparent | — | Polyol | Orange red transparent | — | — |
| J | | Orange red transparent | — | — | Orange red transparent | — | — |
| K | | Orange red transparent | — | — | Orange red transparent | — | — |
| L | | Orange red transparent | — | — | Orange red oil crystallized | ++ (10 days) | VB$_2$ |
| M | | Orange red transparent | — | — | Brown oil crystallized | ++ (30 days) | VB$_2$ |
| N | | Orange red transparent | — | — | Brown oil crystallized | ++ (30 days) | VB$_2$ |
| O | | Orange red transparent | — | — | Orange red oil crystallized | +++ (10 days) | γ-oryzanol |
| P | | Orange red transparent | — | — | Orange red oil crystallized | +++ (10 days) | γ-oryzanol |

EXAMPLE 6

Soft capsules were produced in the same way as in Example 1 from the compositions Q to U prepared in Example 3 and the film-forming agent prepared in Example 4. The resulting soft capsules were stored under the condition of 20° C. and 95% RH for 2 months. The results are shown in Table 9. In the table, "Degree of crystallization" is in accordance with the criterion used in Example 1.

TABLE 9

Results of Storage of Soft Capsules

| Composition | External appearance | Degree and time of crystallization | Microscopic examination |
|---|---|---|---|
| Q | Orange red transparent | — | — |
| R | Orange red transparent | — | — |
| S | Orange red oil crystallized | + (2 months) | γ-oryzanol |
| T | Orange red oil crystallized | ++ (10 days) | VB$_2$ |
| U | Orange red oil crystallized | ++ (10 days) | VB$_2$ |

The above results indicate that the capsules of this invention can be stored stably at room temperature for more than 2 years without crystallization, and that VB$_2$ crystallized out in the capsules for comparison within 1 year of storage.

EXAMPLE 7

Soft capsules were produced in the same way as in Example 1 from the compositions A to H prepared in Example 1 and the film-forming agent prepared as mentioned below.

FILM-FORMING AGENT (1)

Prepared by mixing 116.3 mg of gelatin, 16.3 mg of concentrated glycerin, 1.0 mg of methyl p-hydroxybenzoate, 0.4 mg of propyl p-hydroxybenzoate, and 34.8 mg of sorbitol, and 1.2 mg of purified water.

FILM-FORMING AGENT (2)

Same as above except that 11.6 mg of sorbitol and 39.5 mg of concentrated glycerin were used.

The resulting soft capsules were stored under the condition of 40° C. and 75% RH for 2 months. They remained unchanged in external appearance (yellowish transparent) and microscopic examination, without crystallization.

The soft capsules were also stored under the condition of 20° C. and 95% RH for 2 months. The results are shown in Table 10. In the table, "Degree of crystallization" is in accordance with the criterion used in Example 1.

TABLE 10

Results of Storage of Soft Capsules

| Composition | Film-forming agent | External appearance | Degree and time of crystallization | Microscopic examination |
|---|---|---|---|---|
| A | (1) | Yellowish oil crystallized | + (1 month) | γ-oryzanol |
| B | | Yellowish transparent | — | — |
| C | | Yellowish oil crystallized | ++ (1 month) | γ-oryzanol |
| D | | Yellowish transparent | — | — |
| E | | Yellowish oil crystallized | + (2 months) | γ-oryzanol |
| F | | Yellowish oil crystallized | + (2 months) | γ-oryzanol polyol |
| G | | Yellowish oil crystallized | + (2 months) | γ-oryzanol polyol |
| H | | Yellowish oil crystallized | + (2 months) | γ-oryzanol polyol |
| A | (2) | Yellowish oil crystallized | + (1 month) | γ-oryzanol |
| B | | Yellowish transparent | — | — |
| C | | Yellowish oil crystallized | ++ (1 month) | γ-oryzanol |
| D | | Yellowish transparent | — | — |
| E | | Yellowish oil crystallized | + (2 months) | γ-oryzanol |
| F | | Yellowish oil crystallized | + (2 months) | γ-oryzanol polyol |
| G | | Yellowish oil crystallized | + (2 months) | γ-oryzanol polyol |

TABLE 10-continued

| | | Results of Storage of Soft Capsules | | |
|---|---|---|---|---|
| Composition | Film-forming agent | External appearance | Degree and time of crystallization | Microscopic examination |
| H | | Yellowish oil crystallized | + (2 months) | γ-oryzanol polyol |

The above results indicate that the capsules of this invention can be stored stably at room temperature for a long period of time.

EXAMPLE 8

The compositions V, W, and X to be filled in soft capsules were prepared from γ-oryzanol, $VB_2$, sorbitan sesquioleate, sorbitan monolaurate, sorbitan monooleate, wheat germ oil, and d-α-tocopherol acetate at the ratios shown in Table 11.

Soft capsules of this invention were produced from the compositions V and W in the same way as in Example 1. Also, capsules of this invention were produced from the composition X and two kinds of film-forming agents as used in Example 1 in which the content of sorbitol was changed to 11.7 mg and 34.8 mg and the content of concentrated glycerin was changed to 39.4 mg and 16.3 mg, respectively.

The resulting soft capsules were stored at room temperature for 2 years, and under the condition of 40° C. and 75% RH for 6 months and under the condition of 20° C. and 95% RH for 2 months. The results are shown in Table 12. In the table, "Degree of crystallization" is in accordance with the criterion used in Example 1.

TABLE 11

| | Compositions of Drugs Filled in Soft Capsules | | |
|---|---|---|---|
| | | | (Unit: mg) |
| | Compositions | | |
| Components | V | W | X |
| γ-Oryzanol | 10*1 | 10*2 | 10 |
| $VB_2$ | 10 | 10 | 10 |
| Sorbitan sesquioleate*3 | 50 | 50 | 50 |
| Sorbitan monolaurate*4 | 50 | 50 | — |
| Sorbitan monooleate*5 | — | — | 50 |
| d-α-Tocopherol acetate | 100 | 100 | 100 |
| Wheat germ oil | 120 | 120 | 120 |

*1γ-Oryzanol composed of 50% of campesterol, 25% of β-sitosterol, 15% of cycloartenol, and 10% of 2,4-methylenecycloartanol.
*2γ-Oryzanol composed of 25% of campesterol, 15% of β-sitosterol, 20% of cycloartenol, and 40% of 2,4-methylenecycloartanol.
*3Sorbitan sesquioleate containing 0.9% of total free polyol.
*4Sorbitan monolaurate containing 4.0% of total free polyol.
*5Sorbitan monooleate containing 4.0% of total free polyol.

TABLE 12

| | | Results of Storage of Soft Capsules | | | | | |
|---|---|---|---|---|---|---|---|
| | | Immediately after production | | | After storage | | |
| Composition | Storage condition | External appearance | Degree of crystallization | Microscopic examination | External appearance | Degree and time of crystallization | Microscopic examination |
| V | Room temperature | Orange red transparent | — | — | Orange red transparent | — | — |
| W | | Orange red transparent | — | — | Orange red transparent | — | — |
| X*1 | | Orange red transparent | — | — | Orange red transparent | — | — |
| X*2 | | Orange red transparent | — | — | Orange red transparent | — | — |
| V | 40° C. & 75% RH | Orange red transparent | — | — | Orange red transparent | — | — |
| W | | Orange red transparent | — | — | Orange red transparent | — | — |
| X*1 | | Orange red transparent | — | — | Orange red transparent | — | — |
| X*2 | | Orange red transparent | — | — | Orange red transparent | — | — |
| V | 20° C. & 95% RH | Orange red transparent | — | — | Orange red transparent | — | — |
| W | | Orange red transparent | — | — | Orange red oil crystallized | + (2 months) | γ-oryzanol |
| X*1 | | Orange red transparent | — | — | Orange red transparent | — | — |
| X*2 | | Orange red transparent | — | — | Orange red transparent | — | — |

*1Film-forming agent containing 11.7 mg of sorbitol and 39.4 mg of conc. glycerin.
*2Film-forming agent containing 34.8 mg of sorbitol and 16.3 mg of conc. glycerin.

What we claim is:

1. A soft gelatin capsule which contains a composition encapsulated within said capsule consisting essentially of (a) γ-oryzanol alone or γ-oryzanol in combination with riboflavin butyrate, (b) at least one surface active agent selected from the group consisting of sorbitan monolaureate, sorbitan sesquioleate, and sorbitan monooleate, and (c) at least one oil selected from the group consisting of tocopherol and derivatives thereof, wheat germ oil, safflower oil, soybean oil, neutral oil, cottonseed oil, rapeseed oil, corn oil and peanut oil wherein the γ-oryzanol is the oryzayl alcohol ester of ferulic acid in which the oryzayl alcohol moiety is composed of 25 to 50% of campesterol, 15 to 25.73% of β-sitosterol, 15 to 30% of cycloartenol, and 10 to 40% of 2,4-methylenecycloartanol.

* * * * *